(12) United States Patent
Okunuki et al.

(10) Patent No.: US 8,666,024 B2
(45) Date of Patent: *Mar. 4, 2014

(54) MULTI-X-RAY GENERATING APPARATUS AND X-RAY IMAGING APPARATUS

(71) Applicant: Canon Kabushiki Kaisha, Tokyo (JP)

(72) Inventors: Masahiko Okunuki, Akiruno (JP); Osamu Tsujii, Utsunomiya (JP); Satoshi Shimizu, Great Neck, NY (US); Takashi Ogura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/796,773

(22) Filed: Mar. 12, 2013

(65) Prior Publication Data

US 2013/0202082 A1     Aug. 8, 2013

Related U.S. Application Data

(63) Continuation of application No. 13/166,192, filed on Jun. 22, 2011, now Pat. No. 8,422,637, which is a continuation of application No. 12/394,607, filed on Feb. 27, 2009, now Pat. No. 7,991,120.

(30) Foreign Application Priority Data

Feb. 28, 2008   (JP) ................................ 2008-048827

(51) Int. Cl.
*H01J 35/08*     (2006.01)

(52) U.S. Cl.
USPC .......................... 378/124; 378/134; 378/142

(58) Field of Classification Search
USPC ......... 378/4, 21, 37, 114–116, 119, 121, 122, 378/124, 134, 156, 157
See application file for complete search history.

(56) References Cited

U.S. PATENT DOCUMENTS 6,553,096 B1   4/2003   Zhou et al. .................... 378/122
7,050,537 B2   5/2006   Tsujii .............................. 378/95
(Continued)

FOREIGN PATENT DOCUMENTS

EP     0366372     5/1990
EP     1995757     11/2008
(Continued)

OTHER PUBLICATIONS

Chinese Office Action dated Apr. 26, 2011, concerning Chinese Patent Application No. 200910118644.X, with translation.

(Continued)

*Primary Examiner* — Jurie Yun
(74) *Attorney, Agent, or Firm* — Fitzpatrick, Cella, Harper & Scinto

(57) ABSTRACT

A multi-X-ray generating apparatus which has a plurality of electron sources arranged two-dimensionally and targets arranged at positions opposite to the electron sources includes a multi-electron source which includes a plurality of electron sources and outputs electrons from driven electron sources by selectively driving a plurality of electron sources in accordance with supplied driving signals, and a target unit which includes a plurality of targets which generate X-rays in accordance with irradiation of electrons output from the multi-electron source and outputs X-rays with different radiation qualities in accordance with the generation locations of X-rays. The generation locations and radiation qualities of X-rays from the target unit are controlled by selectively driving the electron sources of the multi-electron source.

7 Claims, 13 Drawing Sheets

(56) References Cited

U.S. PATENT DOCUMENTS

| | | |
|---|---|---|
| 7,104,686 B2 | 9/2006 | Watanabe et al. .............. 378/189 |
| 7,313,225 B2 | 12/2007 | Mertelmeier ................. 378/116 |
| 7,315,606 B2 | 1/2008 | Tsujii .............................. 378/20 |
| 7,359,484 B2 * | 4/2008 | Qiu et al. ...................... 378/122 |
| 7,386,157 B2 | 6/2008 | Tago et al. .................... 382/130 |
| 7,537,385 B2 | 5/2009 | Watanabe et al. .............. 389/189 |
| 7,564,998 B2 | 7/2009 | Tsujii ............................ 382/128 |
| 7,649,981 B2 | 1/2010 | Seppi et al. ................... 378/158 |
| 7,873,146 B2 | 1/2011 | Okunuki et al. .............. 378/122 |
| 7,991,120 B2 * | 8/2011 | Okunuki et al. .............. 378/124 |
| 2005/0084073 A1 | 4/2005 | Seppi et al. ................... 378/156 |
| 2006/0171507 A1 | 8/2006 | Watanabe et al. ............. 378/189 |
| 2007/0009088 A1 * | 1/2007 | Edic et al. ....................... 378/62 |
| 2007/0133747 A1 | 6/2007 | Manak et al. ................... 378/62 |
| 2009/0116613 A1 | 5/2009 | Kataoka et al. ................. 378/47 |
| 2009/0232272 A1 | 9/2009 | Tsujii et al. ..................... 378/16 |
| 2009/0316860 A1 | 12/2009 | Okunuki et al. .............. 378/122 |

FOREIGN PATENT DOCUMENTS

| | | |
|---|---|---|
| JP | S62-211845 | 9/1987 |
| JP | 1-204649 | 8/1989 |
| JP | 5-028939 | 2/1993 |
| JP | 5-036368 | 2/1993 |
| JP | 8-264139 | 10/1996 |
| JP | 9-180894 | 7/1997 |
| JP | 2000-133178 | 5/2000 |
| JP | 2004-511884 | 4/2004 |
| JP | 2004-329784 | 11/2004 |
| JP | 2007-265981 | 10/2007 |
| JP | 2007-278965 | 10/2007 |
| SU | 385209 | 5/1973 |
| WO | 2007/100105 | 9/2007 |

OTHER PUBLICATIONS

J. Zhang, "Stationary Scanning X-ray Source Based on Carbon Nanotube Field Emitters", *Applied Physics Letters 86*, 184104 (2005).

* cited by examiner

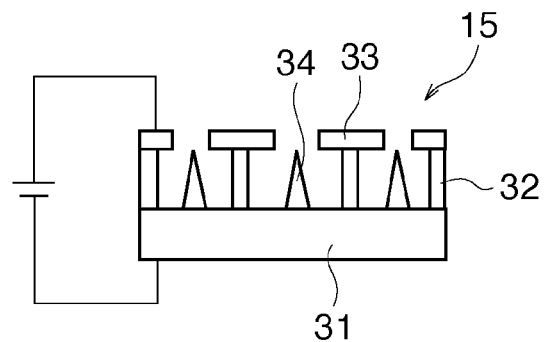
F I G. 3A
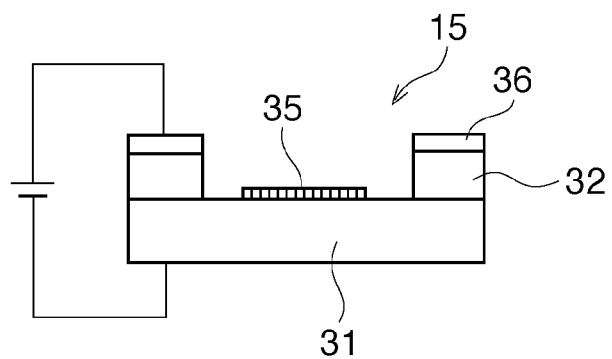
F I G. 3B
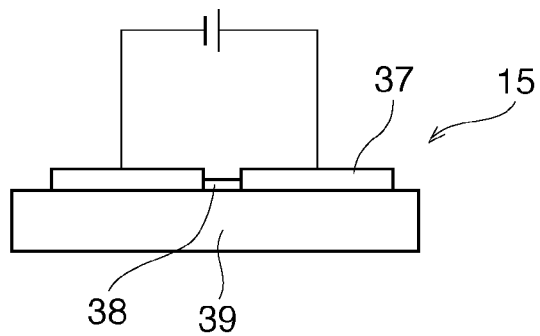
F I G. 3C

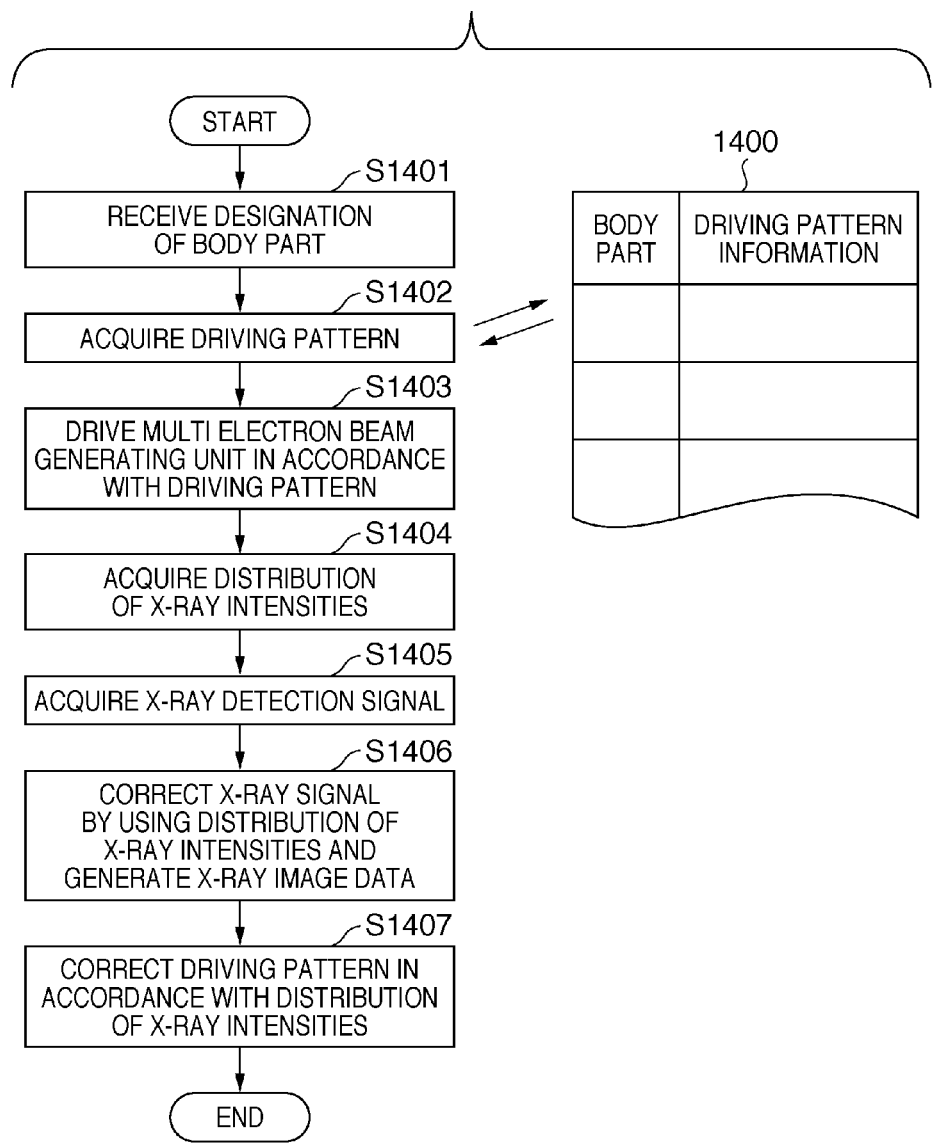

US 8,666,024 B2

MULTI-X-RAY GENERATING APPARATUS AND X-RAY IMAGING APPARATUS

RELATED APPLICATIONS

This application is a continuation of A.N. 13/166,192, filed Jun. 22, 2011, which is a continuation of A.N. 12/394,607, filed Feb. 27, 2009 (now U.S. Pat. No. 7,991,120, issued Aug. 2, 2011), claims benefit of those applications under 35 U.S.C. §120, and claims benefit under 35 U.S.C. §119 of Japanese Patent Application No. 2008-048827, filed Feb. 28, 2008. The entire contents of each of the three mentioned prior applications are incorporated herein by reference.

BACKGROUND OF THE INVENTION

1. Field of the Invention

The present invention relates to a multi-X-ray generating apparatus used for nondestructive radiography, diagnosis, and the like in the fields of medical equipment and industrial equipment which use X-ray sources, and an X-ray imaging apparatus using the multi-X-ray generating apparatus.

2. Description of the Related Art

In general, an X-ray tube uses a thermionic source as an electron source, transmits the thermions from a filament heated to a high temperature to a Wehnelt electrode, extraction electrode, acceleration electrode, and lens electrode, and accelerates an electron beam into a high-energy electron beam. After shaping the electron beam into a desired shape, the X-ray tube generates X-rays by irradiating an X-ray target made of a metal with the beam.

Recently, a cold cathode electron source has been developed as an electron source replacing this thermion source, and has been widely studied as the application of a combination with a flat panel detector (FPD). As a typical cold cathode, a Spindt-type electron source is known, which extracts electrons by applying a high electric field to the tip of a needle with a size of several 10 nm. There are also available, for example, an electron emitter using a carbon nanotube (CNT) as a material and a surface conduction type electron source which emits electrons by forming a nanometer (nm)-order microstructure on the surface of a glass substrate.

Japanese Patent Laid-Open Nos. 09-180894 and 2004-329784 propose, as an application of these electron sources, a technique of extracting X-rays by forming a single electron beam using a Spindt-type electron source or a carbon nanotube type electron source. Japanese Patent Laid-Open No. 08-264139 and *Applied Physics Letters* 86, 184104 (2005), J. Zhang "Stationary Scanning X-Ray Source Based on Carbon Nanotube Field Emitters" disclose a technique of generating X-rays by irradiating an X-ray target with electron beams from a multi-electron source using a plurality of these cold cathode electron sources.

In addition, Japanese Patent Laid-Open No. 2007-265981 discloses an X-ray apparatus which forms X-ray beams from a multi-X-ray source into multi-X-ray beams with excellent characteristics without any mutual interference.

A rotating target type X-ray source is available as a conventional single-focus X-ray source. A method of generating X-rays with different radiation qualities by using this X-ray source has been proposed. As a concrete example of this method, Japanese Patent Laid-Open Nos. 05-028939 and 05-036368 disclose a method of respectively irradiating two types of target materials 102 and 102a placed on one rotating target 101 with electron beams, as shown in FIG. 13. In addition, Japanese Patent Laid-Open No. 01-204649 discloses a method of generating X-rays with different radiation qualities by arranging different target materials on the two surfaces of one rotating target and its applied method.

In a representative rotating target type X-ray source as a single-focus X-ray source, the number of types of radiation qualities which can be obtained from one tube is limited to about two because of restrictions in terms of the shapes of the electron source, target structure, and the like. In addition, since the number of focal spots of the X-ray source is also limited to about two, it is difficult to adjust radiation quality and dose conditions in accordance with a body part of an object and its shape and to obtain an X-ray image with high quality.

SUMMARY OF THE INVENTION

The present invention has been made in consideration of the above problems. Exemplary embodiments of the present invention provide an X-ray generating apparatus and X-ray imaging apparatus which can obtain a high-contrast X-ray image with a low dose at high speed by increasing the degree of freedom in selecting a radiation quality and irradiation position in an X-ray source.

According to one aspect of the present invention, there is provided a multi-X-ray generating apparatus comprising, a multi-electron source which includes a plurality of electron sources arranged two-dimensionally and outputs electrons from driven electron sources by selectively driving the plurality of electron sources in accordance with supplied driving signals; and a target unit which includes a plurality of targets arranged two-dimensionally so as to be opposite to the plurality of electron sources, generates X-rays in accordance with irradiation of electrons output from the multi-electron source, and outputs X-rays with different radiation qualities in accordance with generation locations of X-rays, wherein generation locations and radiation qualities of X-rays from the target unit are controlled by selective driving of electron sources in the multi-electron source.

Also, according to another aspect of the present invention, there is provided an X-ray imaging apparatus comprising, a multi-X-ray generating apparatus defined above; a two-dimensional X-ray detector which generates an electrical signal corresponding to a dose of X-rays which are output from the multi-X-ray generating apparatus and have reached a detection surface; and a driving unit configured to generate a driving signal in accordance with a driving condition and drive each electron source by supplying the driving signal to the multi-electron source.

Further features of the present invention will become apparent from the following description of exemplary embodiments with reference to the attached drawings.

BRIEF DESCRIPTION OF THE DRAWINGS

FIG. 3A is a view showing an example of the arrangement of a Spindt-type element as an example of an electron emitting element;

FIG. 3B is a view showing an example of the arrangement of a carbon nanotube type element as an example of an electron emitting element;

FIG. 3C is a view showing an example of the arrangement of a surface conduction type element as an example of an electron emitting element;

FIG. 14 is a flowchart for explaining radiographic processing performed by a control unit in the fourth embodiment.

DESCRIPTION OF THE EMBODIMENTS

The preferred embodiments of the present invention will be described below with reference to the accompanying drawings.

First Embodiment

Figure 1:
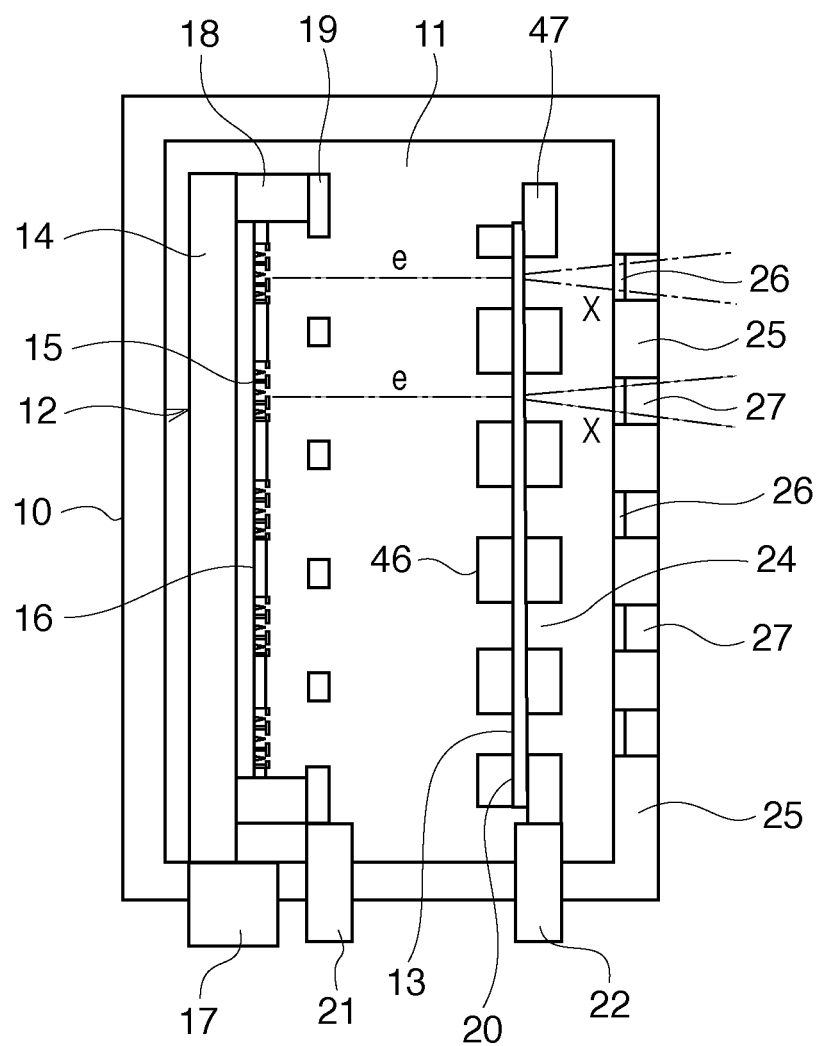
FIG. 1 is a view showing an example of the arrangement of a multi-X-ray generating apparatus according to the first embodiment.

FIG. 1 is a view showing an example of the arrangement of a multi-X-ray generating apparatus 10 as a multi-X-ray source. Referring to FIG. 1, a vacuum chamber 11 incorporates a multi-electron beam generating unit 12 as a multi-electron source and a transmissive target 13 as a multi-X-ray source. The multi-electron beam generating unit 12 includes an element substrate 14 and an element array 16 on which a plurality of electron emitting elements 15 are arrayed. The electron emitting elements 15 function as electron sources. A driving unit 17 controls the driving of the electron emitting elements 15. A lens electrode 19 fixed to an insulator 18 and an anode electrode 20 are provided to control electron beams e emitted from the electron emitting elements 15. High voltages are applied to the lens electrode 19 and the anode electrode 20 via high voltage introducing portions 21 and 22.

The transmissive target 13 on which the generated electron beams e impinge is discretely arranged in accordance with the electron beams e. A vacuum chamber X-ray shield plate 47 made of a heavy metal is provided on the transmissive target 13. The vacuum chamber X-ray shield plate 47 has X-ray extraction portions 24. A wall portion 25 of the vacuum chamber 11 opposite to the X-ray extraction portions 24 is provided with X-ray extraction windows 27 including X-ray transmissive films 26.

The electron beams e emitted from the electron emitting elements 15 receive the lens effect of the lens electrode 19, and are accelerated to the final potential level by portions of the transmissive target 13 of the anode electrode 20. X-ray beams x generated by the transmissive target 13 pass through the X-ray extraction portions 24 and are extracted to the atmosphere via the X-ray extraction windows 27.

Figure 2:
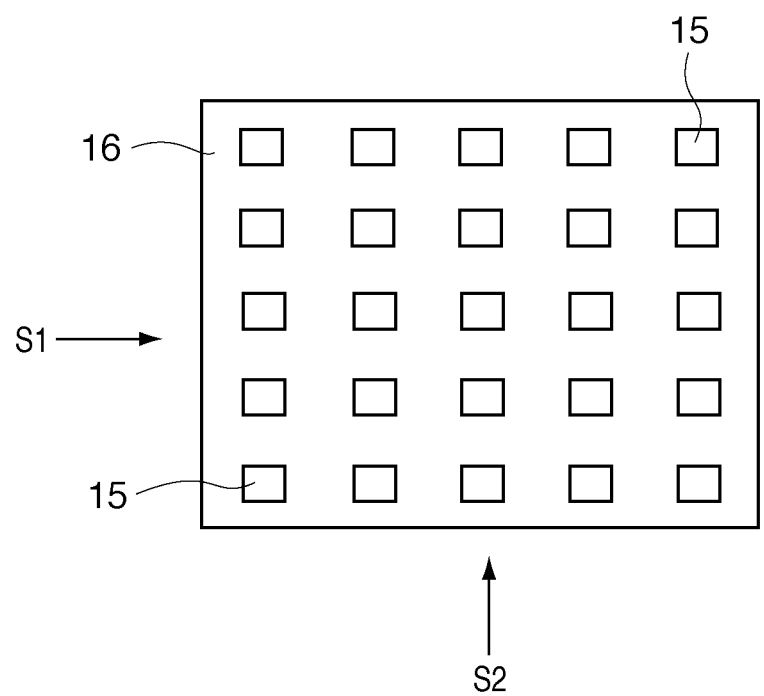
FIG. 2 is a plan view of an element substrate.

The electron emitting elements 15 are two-dimensionally arrayed on the element array 16, as shown in FIG. 2. With recent advances in nanotechnology, it is possible to form a fine structure with nanometer (nm) size at a predetermined position by a device process. The electron emitting elements 15 are manufactured by this nanotechnology. The electron emission amounts of the electron emitting elements 15 are individually controlled by driving signals S1 and S2 (to be described later) via the driving unit 17. That is, individually controlling the electron emission amounts of the electron emitting elements 15 on the element array 16 by using the driving signals S1 and S2 as matrix signals makes it possible to ON/OFF-control each X-ray beam.

FIGS. 3A to 3C are views showing some examples of an element structure which can be used as the electron emitting element 15. FIG. 3A is a view showing the arrangement of the electron emitting element 15 having a conical needle as typified by a Spindt-type electron source. Insulators 32 and extraction electrodes 33 are provided on an element substrate 31 made of Si. Conical emitters 34 each made of a metal or a semiconductor material and having a tip diameter of several tens of nm are formed in nm-size grooves in the centers of the electrodes by using a device manufacturing process.

FIG. 3B is a view showing the arrangement of the carbon nanotube type electron emitting element 15. As a material for an emitter 35, a carbon nanotube having a fine structure of order of several tens of nm is used. The emitter 35 is formed in the center of an extraction electrode 36 on the element substrate 31.

When voltages of several 10 to several 100 V are applied to the extraction electrodes 33 and extraction electrodes 36 of the Spindt-type element and carbon nanotube type element, high electric fields are applied to the tips of the emitters 34 and 35, thereby emitting the electron beams e by the field emission phenomenon.

FIG. 3C is a view showing the arrangement of the surface conduction type electron emitting element 15. A fine structure having nano-particles is formed as an emitter 38 in a gap in a thin-film electrode 37 formed on a glass element substrate 39. When a voltage of 10-odd V is applied between the electrodes of this surface conduction type element, a high electric field is applied to the fine gap formed by fine particles between the electrodes. This generates conduction electrons. At the same time, the electron beams e are emitted in the vacuum, and electron emission can be controlled with a relatively low voltage.

Figure 4:
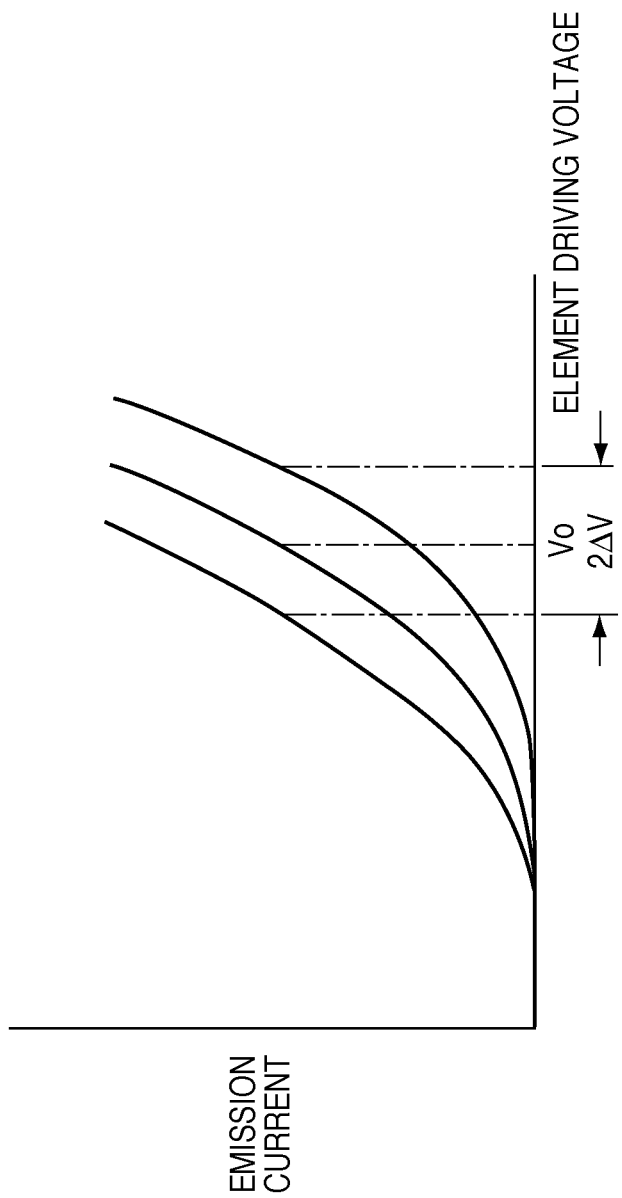
FIG. 4 is a graph showing the voltage-current characteristics of a multi-electron emitting element.

FIG. 4 shows an example of the differences between the voltage-current characteristics of the Spindt-type element, carbon nanotube type element, and surface conduction type element described above with reference to FIGS. 3A to 3C when some of them are used. In order to obtain a constant emission current from each of the plurality of electron emitting elements, the voltage obtained by correcting an average driving voltage Vo with a correction voltage ΔV is applied as a driving voltage to the electron emitting elements 15. This can correct variations in emission currents from the electron emitting elements 15.

Note that the arrangements of the electron emitting elements are not limited those described above. For example, as electron sources for the generation of multi-X-ray beams other than the above electron emitting elements, MIM (Metal Insulator Metal) type elements and MIS (Metal Insulator Semiconductor) type elements can be used. In addition, cold cathode type electron sources of any types such as a semiconductor PN junction type electron source, a Schottky junction type electron source, a carbon-based thin film electron source made of a carbon nanofiber can be used as electron sources for generating multi-X-ray beams.

An X-ray generating apparatus using the above cold cathode type electron emission element as an electron source emits electrons by applying a voltage to the electron emitting element at room temperature without heating the cathode. This apparatus therefore requires no wait time for the generation of X-rays. In addition, since no power is required for heating the cathode, a low-power-consumption X-ray source can be manufactured even by using a multi-X-ray source. Since currents from these electron emitting elements can be ON/OFF-controlled by high-speed driving operation using driving voltages, a multiarray type X-ray source can be manufactured, which can selectively drive an electron emitting element and perform high-speed response operation.

Figure 5A:
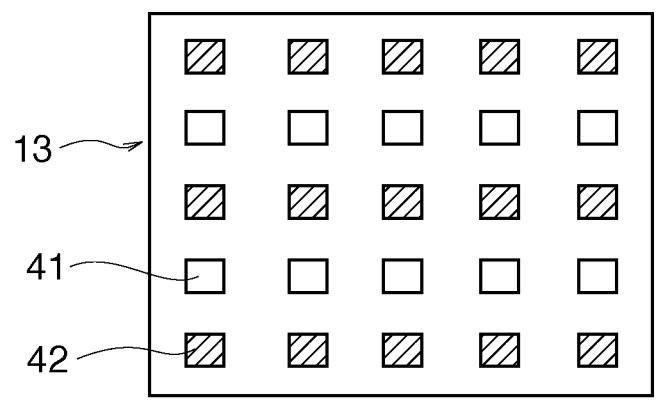
FIG. 5A is a plan view showing an example of the arrangement of a transmissive target using a multi-target.
Figure 5B:
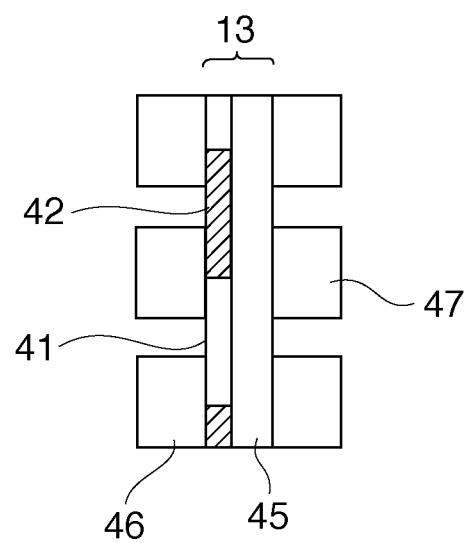
FIG. 5B is a plan view showing an example of the arrangement of a transmissive target using a multi-target.

The transmissive target 13 in this embodiment includes a plurality of targets which generate X-rays in accordance with the irradiation of electrons output from the multi-electron beam generating unit 12 as a multi-electron source, and functions as a target unit which outputs X-rays with different radiation qualities in accordance with the generation locations of X-rays. FIGS. 5A and 5B are views for concretely explaining the arrangement of the multi-X-ray source (target unit), which allows selection of the radiation quality of X-rays to be generated, in the multi-X-ray generating apparatus 10.

FIGS. 5A and 5B are views for explaining the arrangement of the transmissive target 13 according to the first embodiment, and show an example of a multi-target. As shown in FIG. 5A, the transmissive target 13 to which a multi-target is applied has a plurality of targets arranged at positions opposite to the electron emitting elements 15 in FIG. 1. These targets are made of materials different from those for targets A41 and B42. FIG. 5B is a sectional view of the transmissive target 13 shown in FIG. 5A. The targets A41 and B42 are sandwiched between an X-ray/reflected electron beam shield plate 46 and a vacuum chamber X-ray shield plate 47 on a substrate 45. Sandwiching the transmissive target 13 between the X-ray/reflected electron beam shield plate 46 and the vacuum chamber X-ray shield plate 47 in tight contact with each other can efficiently dissipate the heat generated by the targets.

Figure 6:
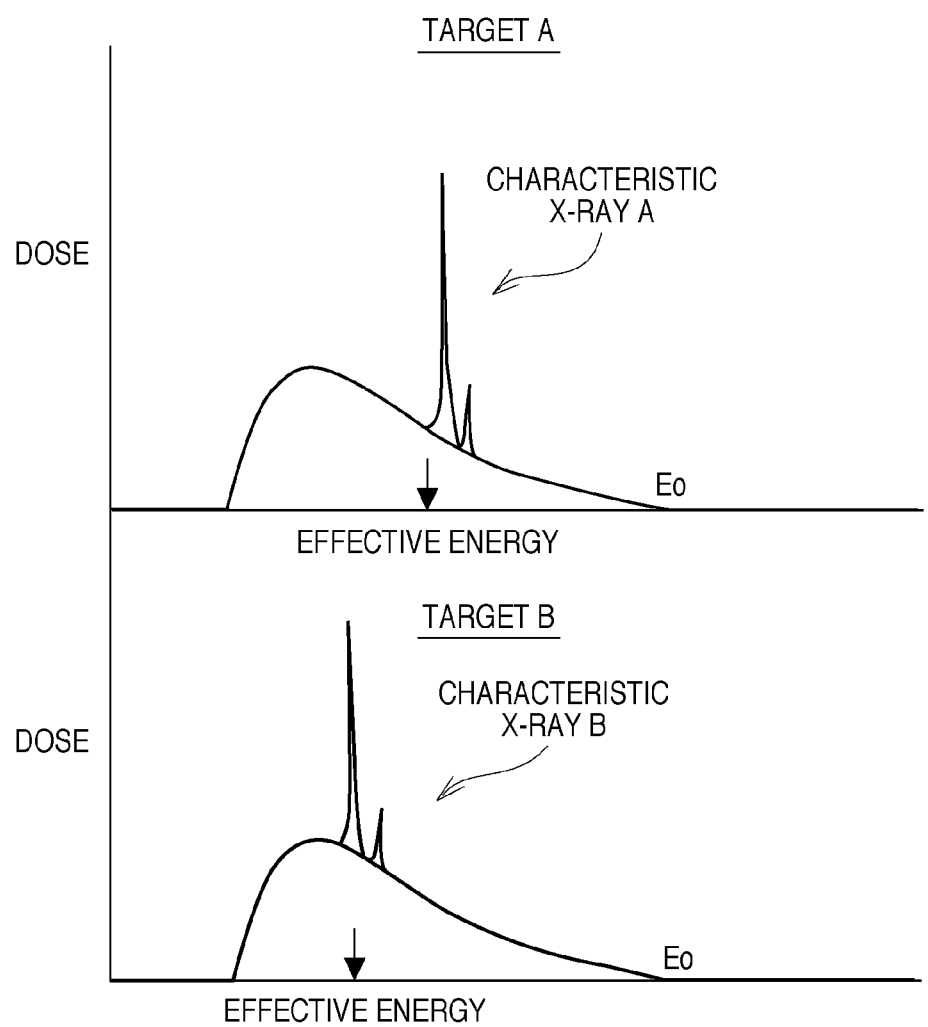
FIG. 6 is a graph showing an example of X-ray spectra in a multi-target scheme.

According to the above arrangement, designating positions where the electron beams e are emitted from the plurality of electron emitting elements 15 can extract X-rays from different types of targets. That is, the transmissive target 13 outputs X-rays with different radiation qualities in accordance with the generation locations of X-rays. The multi-X-ray generating apparatus 10 of this embodiment can therefore generate X-rays having various energy characteristics in one X-ray tube. FIG. 6 is a graph showing X-ray spectra generated by a multi-X-ray generating method using the multi-target in this embodiment in the form of energy vs. dose characteristics. FIG. 6 shows the X-ray spectra generated from the targets A41 and B42. Since a characteristic X-ray A differs in energy from a characteristic X-ray B due to the difference in atomic number between target materials, the radiation qualities of X-rays having different effective energies can be obtained even with the same accelerating voltage (maximum energy Eo) for electron beams. A combination of target materials can be selected from typical combinations of metallic elements such as Cu, Mo, Rh, Pd, Sn, Ta, W, Pt, and Au. Obviously, it suffices to use a combination of other elements or alloys.

The multi-X-ray generating apparatus according to the first embodiment described above can easily obtain a high-quality X-ray image because it can easily select radiation qualities as compared with a method using a conventional X-ray tube.

Second Embodiment

In the first embodiment, the transmissive target 13 which outputs X-rays with different radiation qualities in accordance with the generation locations of X-rays is implemented by a multi-target. The second embodiment exemplifies a case in which such a transmissive target is implemented by a multi-filter in which a plurality of filters having different X-ray absorption characteristics with respect to X-rays are arranged.

Figure 7A:
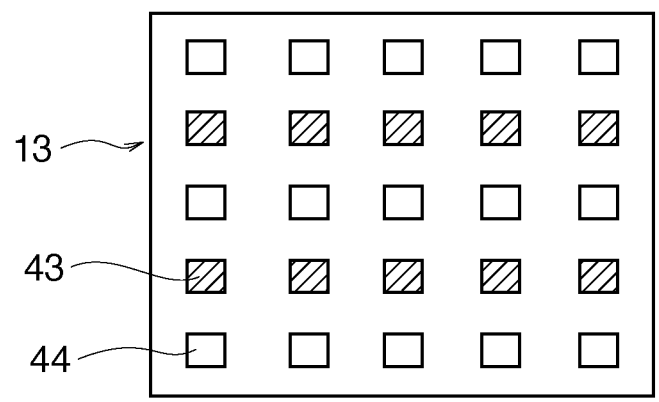
FIG. 7A is a plan view showing an example of the arrangement of a transmissive target using a multi-filter.
Figure 7B:
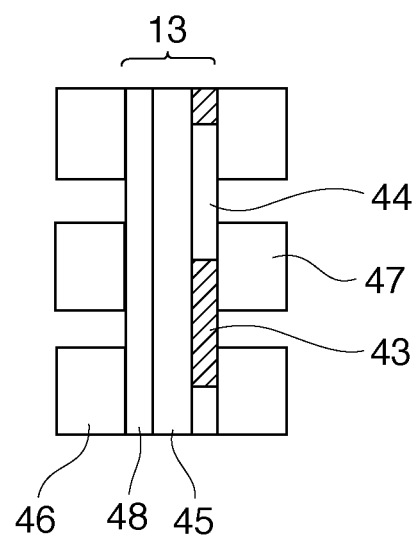
FIG. 7B is a sectional view showing an example of the arrangement of the transmissive target using the multi-filter.

FIGS. 7A and 7B are views showing an example of the arrangement of a transmissive target 13 according to the second embodiment, and show an example using a multi-filter as an X-ray absorbing plate. As shown in FIG. 7A, in the transmissive target 13, filters are independently arranged at target positions opposite to electron emitting elements 15. Filters A43 and B44 are made of different materials. FIG. 7B is a sectional view of the transmissive target 13. The multi-filter including the filters A43 and B44 is arranged on a surface of a substrate 45 which is opposite to a target substrate 48 with which electron beams are irradiated, and the multi-filter is directly sandwiched between a vacuum X-ray shield plate 47 and the substrate 45. This structure can extract X-rays from different filter positions by designating the positions of electron beams e emitted from the electron emitting elements 15. Therefore, one X-ray tube can obtain different X-ray spectra based X-ray absorption characteristic differences by making X-rays generated from the same type of targets pass through the filters A43 and B44.

Figure 8:
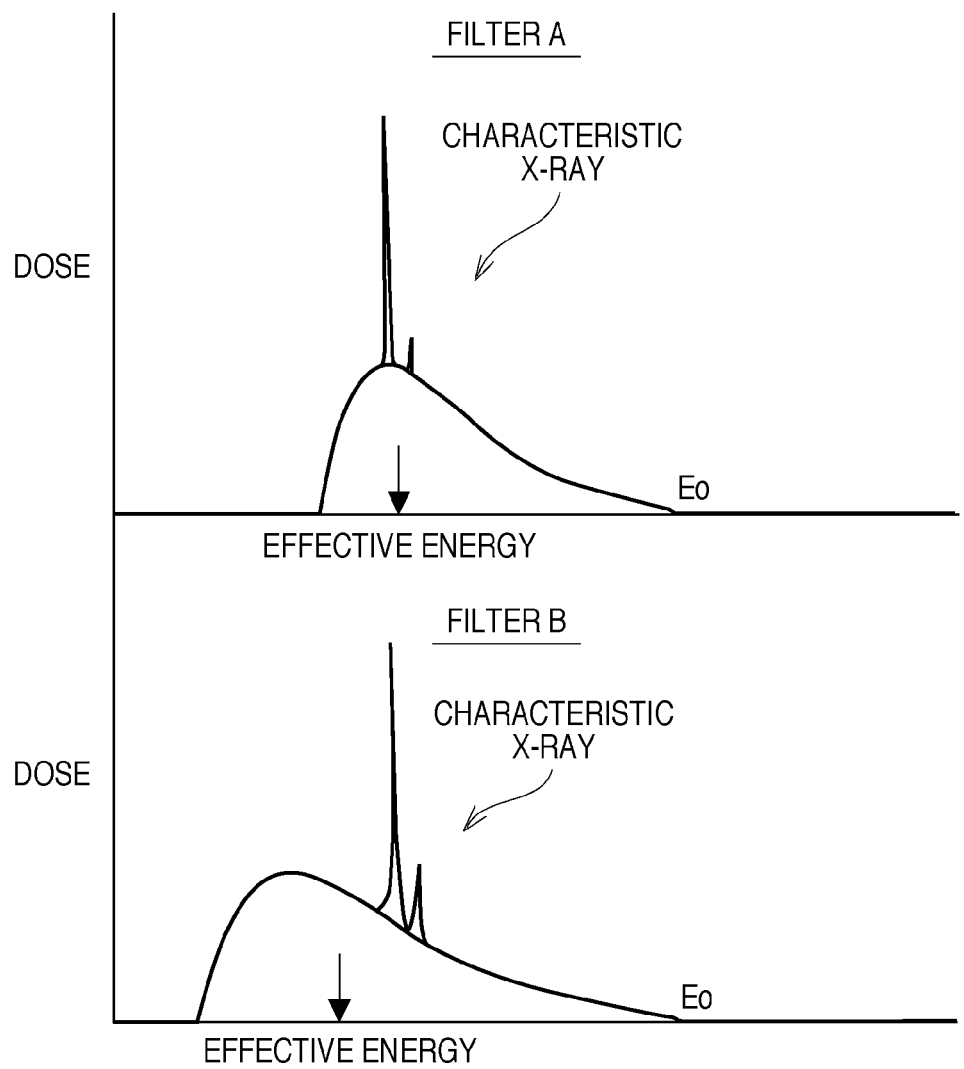
FIG. 8 is a graph showing an example of X-ray spectra obtained by a transmissive target using a multi-filter.

FIG. 8 shows the X-ray spectra obtained by using this multi-filter and, more specifically, the spectra of X-rays transmitted through filters A and B. FIG. 8 shows a case in which a spectrum on a low-energy side is cut by the filters A and B. As shown in FIG. 8, different effective energies can be obtained as those of transmitted X-rays. If Mo and Cu are set as a typical combination of materials for the filters A and B, the filter A cuts a dose on a lower-energy side near a characteristic X-ray ray. In contrast, the filter B cuts a dose from a position slightly apart from the characteristic X-ray. Since materials and their thicknesses can be freely selected for these filters in accordance with a desired spectrum, X-ray spectra having different effective energies can be freely formed by using this multi-filter.

Materials for the above multi-target and multi-filter and a combination of them can be freely set, and it is preferable to combine such materials in accordance with radiographic conditions. In addition, combining the multi-target in the first embodiment with the multi-filter in the second embodiment can generate X-rays with a greater variety of X-ray spectra.

The multi-X-ray generating apparatus according to the second embodiment described above can easily select X-rays with different effective energies (X-rays with different radiation qualities) as compared with the method using the conventional X-ray tube, and hence can easily obtain a high-quality X-ray image.

Third Embodiment

Figure 9:
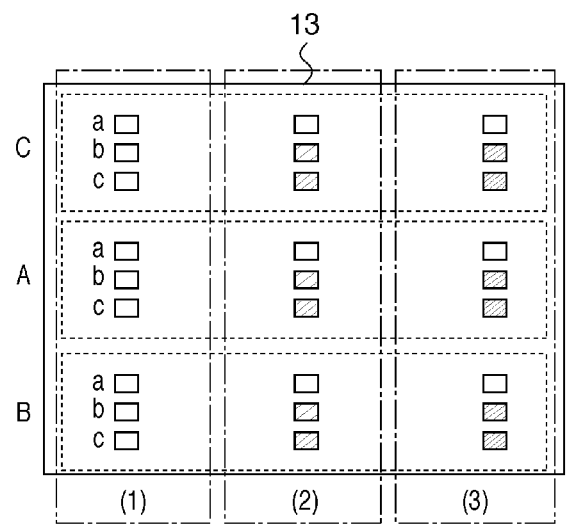
FIG. 9 is a view showing an example of the arrangement of a transmissive target according to the third embodiment.

An application of this X-ray source having a multi-radiation quality characteristic will be described next with reference to FIGS. 9 to 11. FIG. 9 is a view showing a transmissive target 13 according to the third embodiment. This embodiment exemplifies a case in which the transmissive target 13 is formed by combining the multi-target described in the first embodiment with the multi-filter described in the second embodiment.

The transmissive target 13 of the third embodiment is obtained by combining a multi-target with a multi-filter so as to match irradiation conditions for an object. In this case, filters are arrayed in descending order of the radiation quality of X-rays (descending order of effective energy), i.e., in the order (3), (2), and (1). In each of target groups A, B, and C, targets are sequentially arrayed upward (from c to a) in descending order of radiation quality. That is, in the transmissive target 13 shown in FIG. 9, a plurality of different types of targets are periodically arranged. Note that filters having different characteristics can be periodically arranged. For example, as shown in FIG. 9, target groups (1), (2), and (3) are arranged in the order (3)→(2)→(1) in descending order of radiation quality. Different filters may be arranged in the order c→b→a in descending order of radiation quality. Arraying portions which periodically generate different X-rays in target groups in this manner can irradiate an object with X-rays while switching the radiation qualities of X-rays from the respective X-ray sources in accordance with X-ray irradiation conditions.

Figure 10:
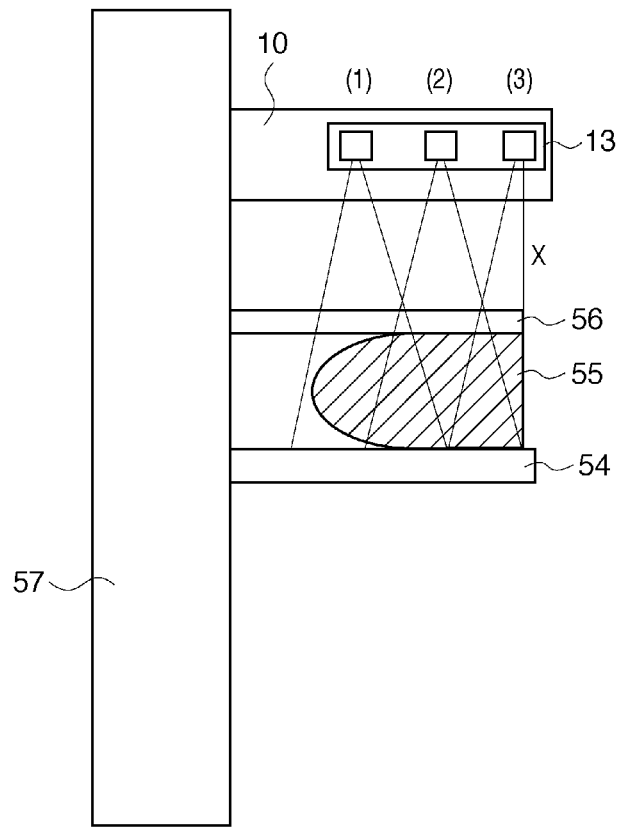
FIG. 10 is a view showing an example of the arrangement of an X-ray imaging apparatus according to the third embodiment.

A multi-X-ray generating apparatus 10 having the above arrangement can be applied to an X-ray imaging apparatus for mammography like that shown in FIG. 10. In this X-ray imaging apparatus, the multi-X-ray generating apparatus 10 having the transmissive target 13 shown in FIG. 9, a two-dimensional X-ray sensor 54, and a compression paddle 56 which compresses an object 55 are mounted on a support base 57. The two-dimensional X-ray sensor 54 is a two-dimensional X-ray detector which generates an electrical signal in accordance with the dose of X-rays reaching the detection surface via the object 55. The X-ray transmission rate of the object 55 increases from the right to the left in FIG. 10. If, therefore, the filters are arrayed ((3)→(1)) so as to decrease the effective energy of X-rays in this direction, the entire irradiation region can be radiographed with an optimal X-ray radiation quality. Radiographing the entire irradiation region with an optimal X-ray radiation quality in this manner is very effective in reducing an exposure dose and obtaining a high-contrast X-ray image.

Figure 11:
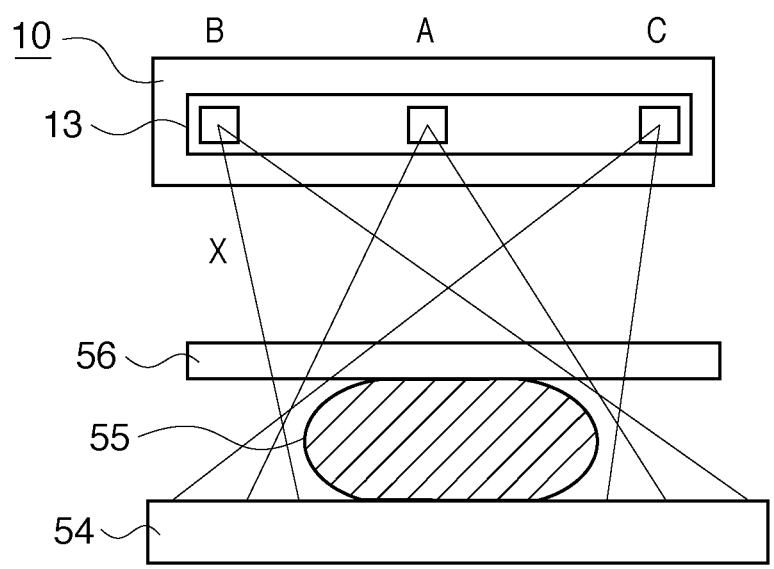
FIG. 11 is a view for explaining the irradiation unit of the X-ray imaging apparatus according to the third embodiment.

FIG. 11 is a view showing the X-ray imaging apparatus in FIG. 10 from another angle and, more specifically, a state in which tomography is performed by using X-rays at different angles from target groups B and C, using the advantage of the multi-X-ray generating apparatus. In this case, since the object is obliquely irradiated with X-rays according to irradiation conditions for the target groups B and C, it is preferable to use an X-ray radiation quality different from that selected for the target group A. The multi-X-ray generating apparatus according to this embodiment can easily implement such X-ray irradiation.

Fourth Embodiment

Figure 12:
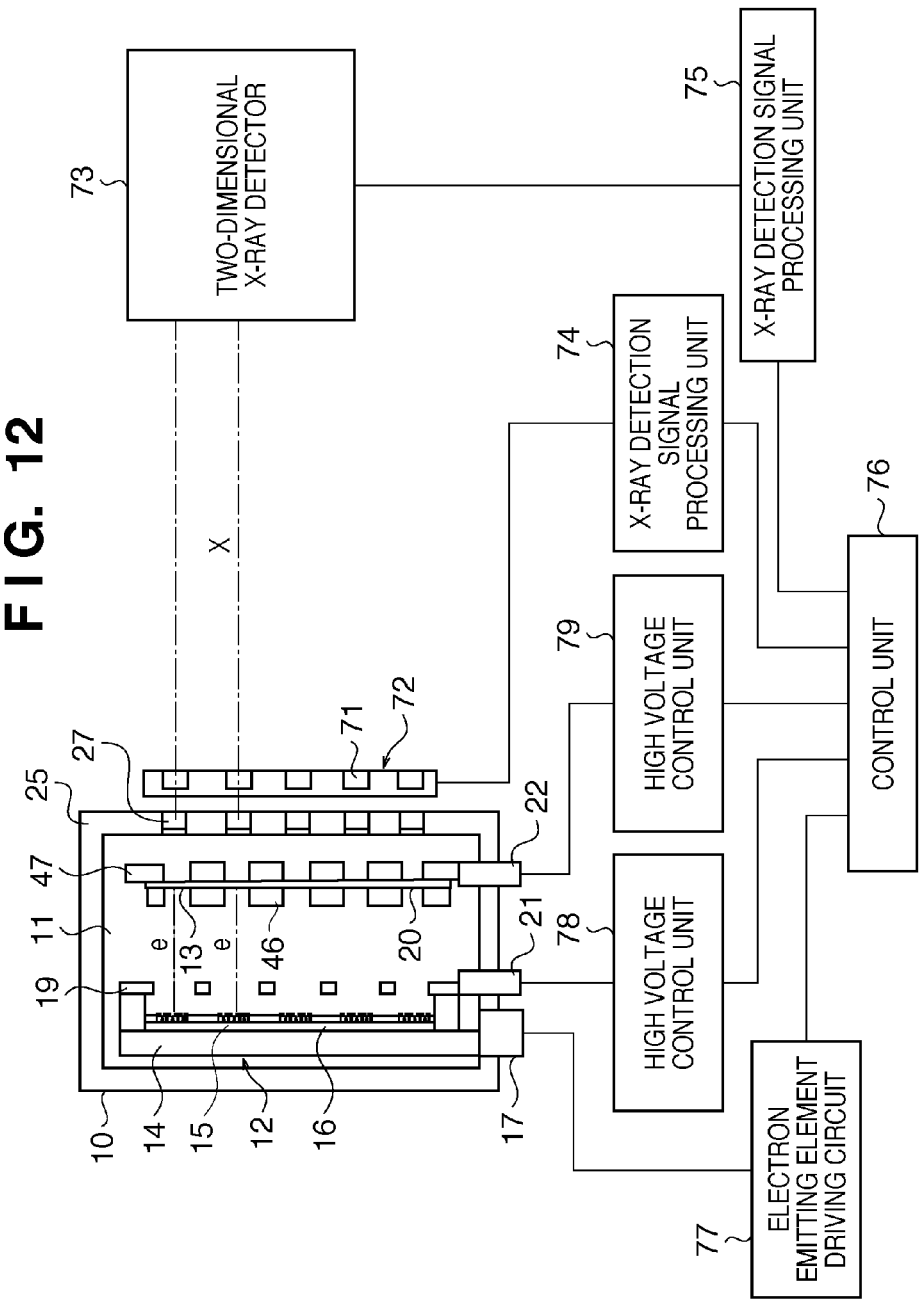
FIG. 12 is a view showing an example of the overall arrangement of a multi-X-ray imaging apparatus according to the fourth embodiment.
Figure 13:
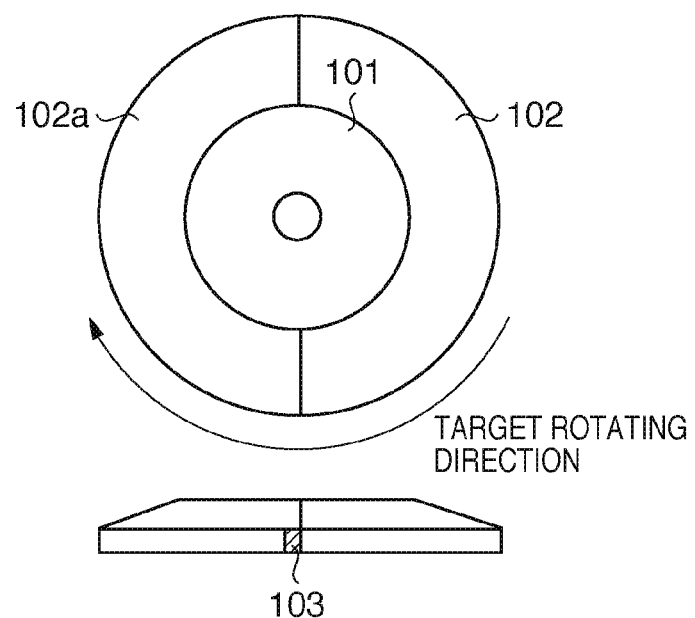
FIG. 13 is a view showing a conventional example of an X-ray generating apparatus which can generate X-rays with different radiation qualities.

FIG. 12 is a view showing an example of the arrangement of a multi-X-ray imaging apparatus including a multi-X-ray generating apparatus 10 having a multi-radiation quality function. In this imaging apparatus, a transmissive X-ray detecting unit 72 including an X-ray intensity measuring unit 71 is arranged in front of the multi-X-ray generating apparatus 10 shown in FIG. 1. This apparatus also includes a two-dimensional X-ray detector 73 which generates an electrical signal corresponding to the dose of X-rays which are output from the multi-X-ray generating apparatus 10 and have reached the detection surface via an object (not shown). The X-ray intensity measuring unit 71 is provided for each X-ray extraction window 27. The transmissive X-ray detecting unit 72 and the two-dimensional X-ray detector 73 are connected to a control unit 76 via X-ray detection signal processing units 74 and 75, respectively. An output of the control unit 76 is connected to a driving unit 17 via an electron emitting element driving circuit 77. Outputs of the control unit 76 are also connected to high voltage introducing portions 21 and 22 of a lens electrode 19 and anode electrode 20 via high voltage control units 78 and 79, respectively.

The X-ray beam x generated from a transmissive target 13 is extracted as multi-X-ray beams x to the atmosphere via X-ray extraction windows 27 provided in a wall portion 25. The X-ray beams x then propagate to the X-ray intensity measuring unit 71. The X-ray beams x are transmitted through the X-ray intensity measuring unit 71 of the transmissive X-ray detecting unit 72, and the object is then irradiated with the X-ray beams x. The two-dimensional X-ray detector 73 detects the X-ray beams x transmitted through the object to obtain an image of the object.

In order to reduce the X-ray dose and obtain a high-contrast image, it is necessary to optimize the radiation quality and dose of X-rays on the basis of object information. The control unit 76 holds driving information for the multi-electron beam generating unit 12 which is used to obtain an optimal contrast with a low dose on the basis of the voltage-current characteristic data of electron emitting elements 15 like those shown in FIG. 4 and the thickness of a body part of an object. The control unit 76 determines driving conditions (the necessity of driving, voltages to be applied, and the like) for the respective electron emitting elements 15 of a multi-electron beam generating unit 12 by referring to the driving information upon receiving information such as the designation of a body part by the user and the thickness of the body part from an input device (not shown). The control unit 76 then controls the electron emitting element driving circuit 77 in accordance with the determined driving conditions. The electron emitting element driving circuit 77 generates driving signals S1 and S2 and supplies them to the driving unit 17 under the control of the control unit 76. In addition, the control unit 76 measures the intensity of actually generated X-rays by using the X-ray intensity measuring unit 71 and the X-ray detection signal processing unit 74, and corrects the driving voltage for each electron emitting element. This makes it possible to capture X-ray images of the respective body parts of the object with settings matching optimal X-ray irradiation conditions.

The control unit 76 corrects each signal from the two-dimensional X-ray detector 73 on the basis of the intensity of X-rays which is the measurement result obtained by the X-ray intensity measuring unit 71. That is, the control unit 76 forms an X-ray image by performing numerical processing of electrical signals corresponding to the doses of X-rays with different radiation qualities on the basis of the measurement result obtained by the X-ray intensity measuring unit 71. When a homogeneous object is radiographed with different radiation qualities, the obtained X-ray images are observed as images with different contrasts because the X-rays with which the object is irradiated have different effective energies. For this reason, this apparatus performs processing for correcting (compressing/enlarging) the contrast range of each acquired image so as to obtain images with the same contrast even with different radiation qualities. This makes it possible to remove the influence of the difference in X-ray radiation quality on X-ray images. If the apparatus does not have the transmissive X-ray detecting unit 72, the control unit 76 may correct each signal from the two-dimensional X-ray detector 73 on the basis of the drive state of each electron emitting element designated by the control unit 76 itself, the voltage vs. current characteristic of each electron emitting element, and the types of targets and filters. That is, the control unit 76 forms X-ray images by performing numerical processing for electrical signals corresponding to a plurality of X-ray doses with different radiation qualities on the basis of the driving conditions for the respective electron sources in the multi-electron source.

FIG. 14 is a flowchart for explaining a sequence of radiographic processing by the control unit 76. In step S1401, the control unit 76 receives the body part designated by the user via an operation unit (not shown). In step S1402, the control unit 76 sets a driving condition (driving pattern) for the multi-electron beam generating unit 12 by referring to the driving information of the multi-electron beam generating unit 12. Body parts and driving conditions (pattern information) are registered in pairs in a driving information table 1400. Specifying a body part can obtain a corresponding driving condition. A driving condition includes ON/OFF information of each of a plurality of electron emitting elements of the multi-electron beam generating unit 12, a voltage (current) to be applied, target/filter information for determining the radiation quality of X-rays, and the like.

In step S1403, the control unit 76 controls the electron emitting element driving circuit 77 to drive the multi-electron beam generating unit 12 under the driving condition acquired in step S1402. In step S1404, the control unit 76 acquires the distribution of X-ray intensities as the measurement result obtained by the X-ray intensity measuring unit 71 in accordance with the above driving operation. In step S1405, the control unit 76 acquires an X-ray detection signal from the X-ray detection signal processing unit 75 as the detection result obtained by the two-dimensional X-ray detector 73 in accordance with the above driving operation. In step S1406, the control unit 76 corrects the X-ray detection signal by using the distribution of X-ray intensities, and generates X-ray image data by using the corrected X-ray detection signal. In step S1407, the control unit 76 corrects a driving condition in the driving information table 1400, as needed, on the basis of the distribution of X-ray intensities. If, for example, there is a difference between a measured X-ray intensity distribution and the X-ray intensity distribution required for the designated body part, the driving condition is corrected to eliminate the difference.

As described above, the X-ray imaging apparatus using the multi-X-ray generating apparatus 10 according to the fourth embodiment sets a driving condition for the electron emitting element driving circuit 77 and an element region to be driven so as to generate an optimal X-ray spectrum in accordance with conditions for an object and its body part. That is, there can be provided an X-ray imaging apparatus including a radiation quality variable type flat panel X-ray source which can designate driving conditions for electron emitting elements in accordance with an object and conditions for its body part.

As has been described above, according to the third and fourth embodiments, it is possible to select X-rays with an optimal radiation quality and irradiate an object with the X-rays in accordance with an X-ray absorption condition and an irradiation angle for each shape information and body part information of an object. This makes it possible to provide an X-ray imaging apparatus which forms a high-contrast X-ray image with a low dose.

According to the present invention, it is possible to increase the degree of freedom in selecting a radiation quality and an irradiation position in an X-ray source.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An X-ray imaging apparatus for mammography comprising:
    a multi-X-ray generating apparatus that generates X-rays at different angles to an object so that tomography is performed; and
    an X-ray detector that generates an electric signal in accordance with a dose of X-rays passing through the object,
    wherein said multi-X-ray generating apparatus comprises:
        a multi-electron source that includes a plurality of electron emitting elements and that emits electrons from a selected electron emitting element among said plurality of electron emitting elements in accordance with a driving signal; and
        a plurality of targets which are connected to a shield member and arranged opposite to said plurality of electron emitting elements and each of which generates X-rays in response to irradiation of electrons emitted from a corresponding one of said electron emitting elements.

2. The apparatus according to claim 1, wherein said shield member comprises at least one of a first shield plate and a second shield plate and said first and second shield plates expose at least a portion of each of said plurality of targets as a generation location of X-rays.

3. The apparatus according to claim 2, wherein said first shield plate shields reflected electrons from said target and said second shield plate shields a part of X-rays generated from said target for extraction of X-rays.

4. The apparatus according to claim 1, further comprising a support base and a compression paddle mounted on said support base to compress the object.

5. The apparatus according to claim 4, wherein said support base mounts said multi-X-ray generating apparatus and an X-ray sensor included in said X-ray detector and
    wherein the object is placed between said compression paddle and said X-ray sensor.

6. The apparatus according to claim 1, wherein said multi-X-ray generating apparatus generates X-rays with different radiation qualities corresponding to the angles to the object.

7. The apparatus according to claim 1, wherein the driving signal is supplied from a driving unit which is controlled by a control unit so that electron emission amounts of said electron emitting elements are individually controlled.

* * * * *